US005273894A

United States Patent [19]

Strauch et al.

[11] Patent Number: 5,273,894

[45] Date of Patent: Dec. 28, 1993

[54] PHOSPHINOTHRICIN-RESISTANCE GENE, AND ITS USE

[75] Inventors: Eckhard Strauch; Wolfgang Wohlleben; Walter Arnold; Renate Alijah; Alfred Pühler, all of Bielefeld; Gerhard Wöhner, Flörsheim am Main; Rüdiger Marquardt, Frankfurt am Main; Susanne Grabley, Königstein/Taunus; Dieter Brauer, Flörsheim am Main; Klaus Bartsch, Kelkheim (Taunus), all of Fed. Rep. of Germany

[73] Assignee: Hoechst Aktiengesellschaft, Frankfurt am Main, Fed. Rep. of Germany

[21] Appl. No.: 795,275

[22] Filed: Nov. 20, 1991

Related U.S. Application Data

[63] Continuation of Ser. No. 605,131, Oct. 31, 1990, abandoned, which is a continuation of Ser. No. 88,118, Aug. 21, 1987, abandoned.

[30] Foreign Application Priority Data

| | | | |
|---|---|---|---|
| Aug. 23, 1986 | [DE] | Fed. Rep. of Germany | 3628747 |
| Nov. 3, 1986 | [DE] | Fed. Rep. of Germany | 3637307 |
| Dec. 16, 1986 | [DE] | Fed. Rep. of Germany | 3642829 |
| Jan. 8, 1987 | [DE] | Fed. Rep. of Germany | 3700313 |

[51] Int. Cl.[5] .................... C12P 13/00; C12N 15/00; C12N 5/00; C12N 15/31; C12N 9/10

[52] U.S. Cl. .................................. 435/129; 435/128; 435/193; 435/172.3; 435/240.4; 435/252.3; 536/23.2; 536/23.7

[58] Field of Search .................... 435/69.1, 91, 172.1, 435/172.3, 193, 320.1, 252.3–252.35, 128, 129, 240.1, 240.4; 536/27, 23.2, 23.7; 800/205; 935/14, 67, 72, 75

[56] References Cited

FOREIGN PATENT DOCUMENTS

| | | | |
|---|---|---|---|
| 0173327 | 3/1986 | European Pat. Off. | 435/172.3 |
| 0242246 | 10/1987 | European Pat. Off. | 435/172.3 |
| 86/02097 | 4/1986 | World Int. Prop. O. | 435/91 |
| 87/05629 | 9/1987 | World Int. Prop. O. | 435/172.3 |

OTHER PUBLICATIONS

Dodds, Plant Genetic Engineering, Cambridge University Press, Cambridge, 1985, pp. 1–3.

Jones, in Dodds, Plant Genetic Engineering, Cambridge University Press, Cambridge, 1985, pp. 269–295.

Gasser et al; Science 244: 1293 (1989).

Vaeck et al; Ciba-Geigy-UCLA Symposium, Tamarron Colo. (1987), Plant Gene Systems and Their Biology, vol. 62: pp. 171 and 174–181.

Wohlleben et al; Gene 70: 25 (1988).

Shah et al; Science 233: 478 (1986).

*Primary Examiner*—James Martinell

*Attorney, Agent, or Firm*—Finnegan, Henderson, Farabow, Garrett & Dunner

[57] ABSTRACT

Selection of *Streptomyces viridochromogenes* DSM 4112 for resistance to phosphinothricyl-alanyl-alanine (PTT) results in PTT-resistance selectants. The DNA fragment which carries the phosphinothricin(PTC)-resistance gene is obtained from the total DNA of these selectants by cutting with BamHI, cloning of a fragment 4.0 kb in size, and selection for PTT resistance. This gene is suitable for the production of PTC-resistant plants, and as a resistance marker and for the selective N-acetylation of the L-form of racemic PTC.

12 Claims, 1 Drawing Sheet

SstII0,55
Tth111I1,6
SstI2,15
PstI2,75
Tth111I2,7
SstI3,9
BamHI0,0
BglII0,95
BglII1,8
SstII2,25
SstII3,55
BamHI4,0
0
1
2
3
4kb

0
PstI
SstII
7,55 SmaI
7,25 XhoI 7,0 SmaI
6,45 BamHI
SmaI 1,6
SstII
pEB2
8,15kb
KpnI 2,5
5,25 SmaI
SstII
tsr
4,95 SmaI
4,65
SstII
ClaI
EcoRV
3,6

SstI
SmaI
PstI
XhoI

SmaI
BamHI
SmaI
KpnI
PstI
pPR1
12,15kb
BglII
EcoRV
tsr
ClaI
BglII
SstII
SmaI
SstII
BamHI
SmaI
SstII

PHOSPHINOTHRICIN-RESISTANCE GENE, AND ITS USE

This application is a continuation of application Ser. No. 07/605,131, filed Oct. 31, 1990, now abandoned, which is a continuation of application Ser. No. 07/088,118, filed Aug. 21, 1987, now abandoned.

Phosphinothricin (PTC, 2-amino-4-methylphosphinobutyric acid) is an inhibitor of glutamine synthetase. PTC is a "structural unit" of the antibiotic phosphinothricylalanyl-alanine. This tripeptide (PTT) is active against Gram-positive and Gram-negative bacteria as well as against the fungus *Botrytis cinerea* (Bayer et al., Helv. Chim. Acta 55 (1972) 224). PTT is produced by the strain *Streptomyces viridochromogenes* Tü 494 (DSM 40736, DSM 4112).

German Patent 2,717,440 discloses that PTC acts as a total herbicide. The published PCT Application WO 86/02097 describes plants whose resistance to PIC is attributable to overproduction of glutamine synthetase. Overproduction of this type, for example resulting from gene amplification, entails the risks of instability. Hence, such an instability would be associated with a decrease in the overproduction of glutamine synthetase, and the competitive inhibitory action of PTC would reappear.

In contrast, the invention, which is defined in the patent claims, relates to a PTC-resistance gene and to its use for the production of PTC-resistant plants. In addition, this gene can also be used as a resistance marker. Furthermore, the gene is suitable for the selective N-acetylation of the L-form of racemic PTC.

Figure 1:
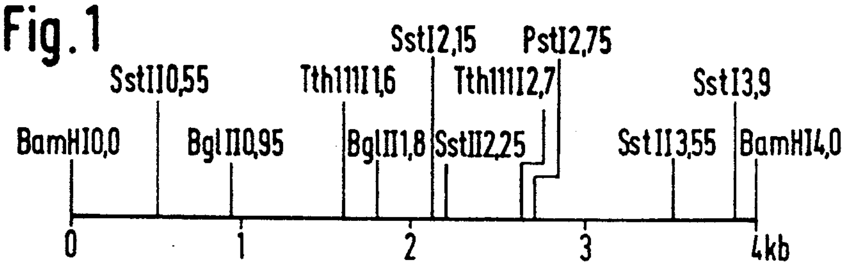
FIG. 1 is a restriction map of a 4.0 kb fragment of DNA from S. viridochromogenes DSM 4112.

The PTC-resistance gene according to the invention can be obtained by cutting, with BamHI, the total DNA from Streptomyces viridochromogenes DSM 4112 which has been selected for PTT resistance, by cloning a fragment 4.0 kb in size, and by selection for PTT resistance. The restriction map (FIG. 1) details the characteristics of this 4.0 kb fragment.

Cloning experiments on sections of this 4 kb fragment were carried out to localize the position of the coding region more accurately. It emerged from this that the resistance gene is located on the 1.6 kb SstII-SstI fragment (positions 0.55 to 2.15 in FIG. 1). Digestion with BglII resulted in the fragment which is 0.8 kb in size and which, after incorporation into a plasmid and transformation of *S. lividans*, confers PTT resistance. This resistance is caused by N-acetylation of PTC.

Maxam and Gilbert sequencing of the 0.8 kb fragment reveals DNA sequence I (Annex). The position of the resistance gene can be determined from the open reading frame of this sequence (from position 258). The end of the gene is located at the penultimate nucleotide shown (position 806), i.e. the last nucleotide (position 807) is the first of the stop codon.

The Shine-Dalgarno sequence in DNA sequence I is emphasized by underlining, as is the GTG acting as start codon. Thus, the top line depicts the definitive reading frame.

DNA sequence II shows the restriction sites within the sequenced gene. Enzymes which cut the sequence more than six times are not indicated.

The antibiotic PTT is taken up by bacteria and broken down to PTC. The latter also inhibits glutamine synthetase in bacteria, so that the bacteria die of a lack of glutamine. Hence, PTT-producing bacteria ought to have a mechanism which protects them from the action of PTT, that is to say either prevents reuptake of the PTT which has been produced or permits a modification of the breakdown product PTC. However, surprisingly, the PTT producer *S. viridochromogenes* DSM 4112 is sensitive to its own antibiotic. Unexpectedly, it proved possible, however, by selection for PTT resistance to find, at the surprisingly high rate of $10^{-5}$, selectants which are resistant to PTT and, moreover, suppress the background growth of adjacent colonies.

A gene bank was set up from the DNA of these selectants by isolating the DNA and cleaving it with BamHI and ligating it into a Streptomycetes vector. The ligation mixture was transformed into the commercially available strain *S. lividans* TK 23, resulting in about 5000 to 10000 transformants having an insert of about 1 to 5 kb per 1 μg of ligation mixture. Among the transformants there were PTT-resistant *S. lividans* strains. It was possible, by isolation of the plasmids and retransformation into *S. lividans*, to show that the resistance is plasmid-coded. The gene responsible for the resistance is located on a 4 kb BamHI fragment (FIG. 1). The coding region is located on the 0.8 kb BglII fragment. The BamHI fragment contains no cleavage sites for the enzymes ClaI, EcoRI, EcoRV, HindIII, HpaI, KpnI, PvuI, PvuII and XhoI.

Comparison with the restriction map of a resistance gene, which has not been characterized in detail, for *S. hygroscopicus* FERM BP-130/ATCC 21705 (European Patent Application with the publication no. 0,173,327, FIG. 7) shows that the resistance gene according to the invention differs from the known gene, which was found during the search for PTT biosynthesis genes.

It was possible to show, by incubation of cell extracts from *S. viridochromogenes* DSM 4112 and *S. lividans* TK 23 on the one hand, and the PTT-resistant *S. viridochromogenes* selectants and a plasmid-carrying *S. lividans* transformant, on the other hand, with PTC and acetyl-coenzyme A that the latter cells have acetylating activity. Chromatography tests show that the acetylation takes place on the amino group.

Since PTT-resistance has also been found in *E. coli*, and thus the resistance mechanism also functions in Gram-negative bacteria, it is possible to rule out resistance based on transport phenomena. Thus, after coupling to plant promoters and using suitable vectors, the resistance gene according to the invention can be transformed into plants, and in this way PTC-resistant plants can be produced.

The N-acetylation of PTC can also be used for racemate resolution of synthetic D,L-PTC since selective acetylation of only the L-form takes place.

Thus the invention also relates to the use of the resistance gene for the selective N-acetylation of the L-form of racemic PTC.

The PTC acetyltransferase coded for by the resistance gene according to the invention can thus be used to separate racemic PTC, as can be obtained, for example, by the method of German Patent 2,717,440, into the optical antipodes by exposing the racemate to the acetylating action of this enzyme, since there is selective attack on the L-form while the D-form remains unchanged. The mixture thus obtained can then be fractionated in a manner known per se on the basis of the differences in properties.

The contacting of N-acyl-D,L-amino acids with acylases, which are immobilised on carriers where appropriate, with selective liberation of the L-amino acid, which can be extracted with water-immiscible solvents from the mixture with the N-acyl-D-amino acid after acidification, has been disclosed (British Patent 1,369,462). A corresponding fractionation of N-acyl-D,L-PTC is disclosed, for example, in German Offenlegungsschrift 2,939,269 or U.S. Pat. No. 4,226,941.

The D-PTC which remains according to the invention can be racemized in known manner (European Patent Application with the publication no. (EP-A) 0,137,371, example 8), and then returned to the process.

It is possible, but not necessary, to isolate the enzyme, this also being intended to mean, here and hereinafter, always the enzymatically active part. If the enzyme is isolated, it can be used in the free form or the form immobilised on a carrier. Examples of suitable carriers are described in EP-A 0,141,223. However, it is expedient not to isolate the enzyme but to use any desired PTC-resistant cells which express the enzyme according to the invention. Thus, it is possible and expedient to use the PTT-resistant selectants of *S. viridochromogenes* DSM 4112. Moreover, it is possible and advantageous to use any desired cell which has been transformed with the gene according to the invention and which is able to express PTC acetyltransferase. In this connection, the gene according to the invention, this also being intended to mean active parts thereof, can be introduced into the host cell in plasmid-integrated form or by using other customary methods of gene manipulation, for example by transfection. For example, incorporation into a *E. coli* expression plasmid and transformation of *E. coli* with such a plasmid is expedient, for example by the methods known from EP-A 0,163,249 and 0,171,024.

For the N-acetylation, according to the invention, of L-PTC in the racemate the cells which express PTC acetyltransferase can be used in the free or immobilised form, with the customary methods of immobilisation being used (for example German Offenlegungsschrift 3,237,341 and Literature cited therein).

The enzymatic acetylation, according to the invention, of L-PTC is carried out in the manner customary for enzymatic reactions, with the conditions of the method being governed by the characteristics of the organism used. In principle, methods suitable for this are the same as for the abovementioned selective deacylation method.

The invention is illustrated in detail in the examples which follow. Unless otherwise stated, parts and percentage data relate to weight.

EXAMPLE 1

PTT-resistant selectants

The strain *S. viridochromogenes* DSM 4112 was cultured on minimal medium (Hopwood et al., Genetic Manipulation of Streptomyces, A Laboratory Manual, The John Innes Foundation, Norwich, England (1985), page 233) and increasing concentrations of PTT were added. At a concentration of 100 μg/ml one resistant colony was found per $10^5$ colonies, approximately.

EXAMPLE 2

Preparation of the vector

Figure 2:
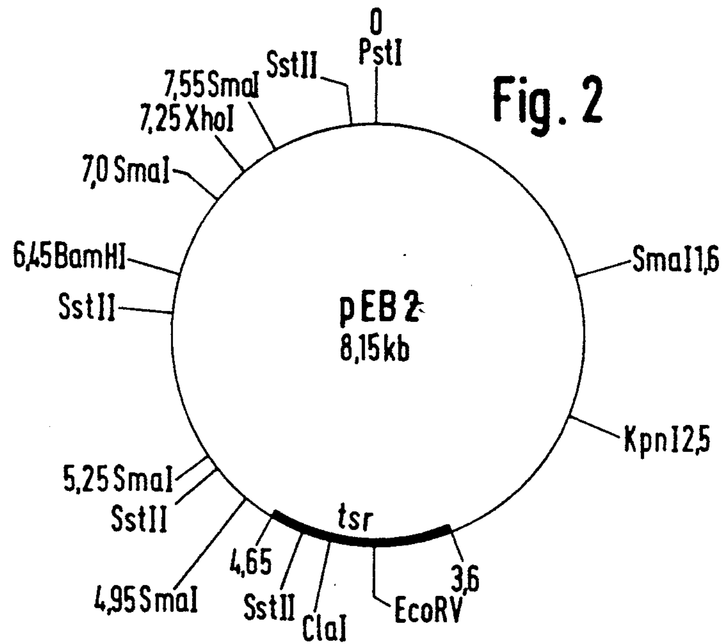
FIG. 2 is a restriction map of pEB2.

The plasmid pSVH1 (European Patent 0,070,522; U.S. Pat. No. 4,673,642) is cut with BglII, and the fragment about 7.1 kb in size is isolated and ligated with the 1.1 kb BclI fragment having thiostrepton resistance (European Patent Application with the publication number 0,158,201). The plasmid pEB2 which is about 8.15 kb in size is obtained (FIG. 2).

EXAMPLE 3

Isolation of the resistance gene

Figure 3:
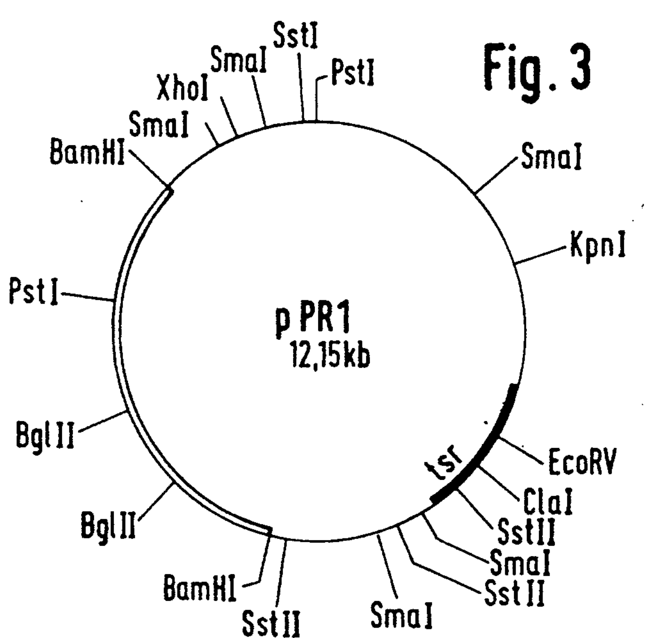
FIG. 3 is a restriction map of pPR1.

The total DNA is isolated from the selectants obtained in example 1, and it is cleaved with BamHI. The plasmid pEB2 is likewise opened with BamHI, and the two mixtures are combined and ligated. The ligation mixture is transformed into *S. lividans* TK 23 (obtainable from the John Innes Foundation), with 5000 to 10000 transformants having an insert of about 1-5 kb being obtained per 1 μg of ligation mixture. Selection for PTT-resistance produces two resistant *S. lividans* colonies. The plasmid which has been taken up is isolated from the latter and is cut with BamHI. A 4 kb BamHI fragment which carries the gene responsible for resistance is found. This plasmid was called pPR1 (FIG. 3).

Retransformation into *S. lividans* TK 23 shows, that the PTT-resistance is plasmid-coded, since the transformants grow on minimal medium containing 100 μg/ml PTT.

EXAMPLE 4

Demonstration of the inactivation of PTC by N-acetylation

The following strains were examined to demonstrate the acetylating activity of the cloned fragment: *S. viridochromogenes* DSM 40736, *S. viridochromogenes* (PTT-resistant mutant), *S. lividans* TK23 and *S. lividans* TK 23 (pPR1).

This entails the strains being inoculated into lysis medium A (European Patent Application with the publication number 0,158,872, page 6) and incubated at 30° C. in an orbital shaker for 2 days. After harvesting, 1 mg of mycelium is disrupted with ultrasound in a suitable buffer (for example RS buffer: C. J. Thompson et al., J. Bacteriol. 151 (1982), 678-685). The procedure for a typical experiment to measure PTC breakdown is as follows:

100 μl of PTC solution (250 μg/ml) and 50 μl of acetyl-CoA (4 mg/ml) are added to 250 μl of crude extract, and the mixture is incubated at 30° C. for 2 hours. The amounts of PTC which are still present after this time are measured by HPLC. The results of this are as follows:

| Strain | unreacted PTC / introduced PTC |
|---|---|
| *S. lividans* TK23 | 100% |
| *S. viridochromogenes* (DSM 40736) | 72% |
| *S. viridochromogenes* Selectant | 7% |
| *S. lividans* TK23 (pPR1) | 31% |

A comparison with reference substances on thin-layer chromatography (no stain with ninhydrin) demonstrates that N-acetylation of the PTC has taken place.

DNA Sequence I

```
IleTrpSerAspValLeuGlyAlaGlyProValLeuProGlyAspAspPhePheSerLeuGlyGlyThrSerIle
AspLeuGluArgArgProGlyGlyArgSerGlyAlaAlaArgGlyArgLeuLeuLeuProArgArgHisLeuHis
ArgSerGlyAlaThrSerTrpGlyProValArgCysCysProGlyThrThrSerSerProSerAlaAlaProPro
AGATCTGGAGCGACGTCCTGGGGGCCGGTCCGGTGCTGCCCGGGGACGACTTCTTCTCCCTCGGCGGCACCTCCA   75
TCTAGACCTCGCTGCAGGACCCCCGGCCAGGCCACGACGGGCCCCTGCTGAAGAAGAGGGAGCCGCCGTGGAGGT
SerArgSerArgArgGlyProProArgAspProAlaAlaArgProArgSerArgArgGlyArgArgCysArgTrp
AspProAlaValAspGlnProGlyThrArgHisGlnGlyProValValGluGluGlyGluAlaAlaGlyGlyAsp
IleGlnLeuSerThrArgProAlaProGlyThrSerGlyProSerSerLysLysGluArgProProValGluMet

SerAlaLeuArgValValSerArgIleArgLysGluLeuGlyValProLeuArgLeuAlaValIlePheGluThr
LeuGlyValAlaGlyGlyLeuAlaHisProGlnGlyThrArgArgAlaThrProAlaArgArgAspLeuArgAsp
SerArgArgCysGlyTrpSerArgAlaSerAlaArgAsnSerAlaCysHisSerGlySerProOP SerSerArg
TCTCGGCGTTGCGGGTGGTCTCGCGCATCCGCAAGGAACTCGGCGTGCCACTCCGGCTCGCCGTGATCTTCGAGA   150
AGAGCCGCAACGCCCACCAGAGCGCGTAGGCGTTCCTTGAGCCGCACGGTGAGGCCGAGCGGCACTAGAAGCTCT
ArgProThrAlaProProArgAlaCysGlyCysProValArgArgAlaValGlyAlaArgArgSerArgArgSer
ArgArgGlnProHisAspArgAlaAspAlaLeuPheGluAlaHisTrpGluProGluGlyHisAspGluLeuArg
GluAlaAsnArgThrThrGluArgMetArgLeuSerSerProThrGlySerArgSerAlaThrIleLysSerVal

ProSerLeuGluAlaValAlaGluSerValLeuArgGluLeuLysGlyThrAM OC ArgGlyAlaArgHisPro
AlaValProGlySerGlyGlyArgIleArgThrProArgThrGluGlyAspValValLysArgCysProProPro
ArgArgProTrpLysArgTrpProAsnProTyrSerAlaAsnOP ArgGlyArgSerLysGluValProAlaThr
CGCCGTGGGTGGAAGCGGTGGCCGAATCCGTACTCCGCGAACTGAAGGGGACGTAGTAAAGAGGTGCCCGCCACC   225
GCGGCAGGGACCTTCGCCACCGGCTTAGGCATGAGGCGCTTGACTTCCCCTGCATCATTTCTCCACGGGCGGTGG
AlaThrGlyProLeuProProArgIleArgValGlyArgValSerProSerThrThrPheLeuHisGlyGlyGly
ArgGlyGlnPheArgHisGlyPheGlyTyrGluAlaPheGlnLeuProArgLeuLeuSerThrGlyAlaValArg
GlyAspArgSerAlaThrAlaSerAspThrSerArgSerSerPheProValTyrTyrLeuProAlaArgTrpGly

LeuSerGlnAsnThrGluGlyArgProHisValSerProGluArgArgProValGluIleArgProAlaThrAla
AlaPheAlaGluHisArgArgLysThrThrArgGluProArgThrThrProGlyArgAspProSerArgHisArg
ArgPheArgArgThrProLysGluAspHisThrOP AlaGlnAsnAspAlaArgSerArgSerValProProPro
CGCTTTCGCAGAACACCGAAGGAAGACCACACGTGAGCCCAGAACGACGCCCGGTCGAGATCCGTCCCGCCACCG   300
GCGAAAGCGTCTTGTGGCTTCCTTCTGGTGTGCACTCGGGTCTTGCTGCGGGCCAGCTCTAGGCAGGGCGGTGGC
AlaLysAlaSerCysArgLeuPheValValArgSerGlyLeuValValGlyProArgSerGlyAspArgTrpArg
LysArgLeuValGlyPheSerSerTrpValHisAlaTrpPheSerAlaArgAspLeuAspThrGlyGlyGlyGly
SerGluCysPheValSerProLeuGlyCysThrLeuGlySerArgArgGlyThrSerIleArgGlyAlaValAla

AlaAspMetAlaAlaValCysAspIleValAsnHisTyrIleGluThrSerThrValAsnPheArgThrGluPro
ArgArgHisGlyGlyGlyLeuArgHisArgGlnSerLeuHisArgAspGluHisGlyGlnLeuProTyrGlyAla
ProProThrTrpArgArgSerAlaThrSerSerIleThrThrSerArgArgAlaArgSerThrSerValArgSer
CCGCCGACATGGCGGCGGTCTGCGACATCGTCAATCACTACATCGAGACGAGCACGGTCAACTTCCGTACGGAGC   375
GGCGGCTGTACCGCCGCCAGACGCTGTAGCAGTTAGTGATGTAGCTCTGCTCGTGCCAGTTGAAGGCATGCCTCG
ArgArgCysProProProArgArgCysArgOP AspSerCysArgSerSerCysProOP SerGlyTyrProAla
GlyValHisArgArgAspAlaValAspAspIleValValAspLeuArgAlaArgAspValGluThrArgLeuArg
AlaSerMetAlaAlaThrGlnSerMetThrLeuOP AM MetSerValLeuValThrLeuLysArgValSerGly

GlnThrProGlnGluTrpIleAspAspLeuGluArgLeuGlnAspArgTyrProTrpLeuValAlaGluValGlu
AlaAspSerAlaGlyValAspArgArgProGlyAlaProProGlyProLeuProLeuAlaArgArgArgGlyGly
ArgArgLeuArgArgSerGlySerThrThrTrpSerAlaSerArgThrAlaThrProGlySerSerProArgTrp
CGCAGACTCCGCAGGAGTGGATCGACGACCTGGAGCGCCTCCAGGACCGCTACCCCTGGCTCGTCGCCGAGGTGG   450
GCGTCTGAGGCGTCCTCACCTAGCTGCTGGACCTCGCGGAGGTCCTGGCGATGGGGACCGAGCAGCGGCTCCACC
AlaSerGluAlaProThrSerArgArgGlyProAlaGlyGlyProGlySerGlyArgAlaArgArgArgProPro
LeuSerArgLeuLeuProAspValValGlnLeuAlaGluLeuValAlaValGlyPRoGluAspGlyLeuHisLeu
CysValGlyCysSerHisIleSerSerArgSerArgArgTrpSerArgAM GlyGlnSerThrAlaSerThrSer
```

-continued

DNA Sequence I

```
    GlyValValAlaGlyIleAlaTyrAlaGlyProTrpLysAlaArgAsnAlaTyrAspTrpThrValGluSerThr
  GlyArgArgArgArgHisArgLeuArgArgProLeuGluGlyProGlnArgLeuArgLeuAspArgArgValAsp
ArgAlaSerSerProAlaSerProThrProAlaProGlyArgProAlaThrProThrThrGlyProSerSerArg
AGGGCGTCGTCGCCGGCATCGCCTACGCCGGCCCCTGGAAGGCCCGCAACGCCTACGACTGGACCGTCGAGTCGA     525
TCCCGCAGCAGCGGCCGTAGCGGATGCGGCCGGGGACCTTCCGGGCGTTGCGGATGCTGACCTGGCAGCTCAGCT
ProArgArgArgArgCysArgArgArgArgGlyArgSerProGlyCysArgArgArgSerSerArgArgThrSer
    AlaAspAspGlyAlaAspGlyValGlyAlaGlyProLeuGlyAlaValGlyValValProGlyAspLeuArgArg
  ProThrThrAlaProMetAlaAM AlaProGlyGlnPheAlaArgLeuAlaAM SerGlnValThrSerAspVal

    ValTyrValSerHisArgHisGlnArgLeuGlyLeuGlySerThrLeuTyrThrHisLeuLeuLysSerMetGlu
  GlyValArgLeuProProAlaProAlaAlaArgThrGlyLeuHisProLeuHisProProAlaGluValHisGly
ArgCysThrSerProThrGlyThrSerGlySerAspTrpAlaProProSerThrProThrCysOP SerProTrp
CGGTGTACGTCTCCCACCGGCACCAGCGGCTCGGACTGGGCTCCACCCTCTACACCCACCTGCTGAAGTCCATGG     600
GCCACATGCAGAGGGTGGCCGTGGTCGCCGAGCCTGACCCGAGGTGGGAGATGTGGGTGGACGACTTCAGGTACC
ProThrArgArgGlyGlyAlaGlyAlaAlaArgValProSerTrpGlyArgCysGlyGlyAlaSerThrTrpPro
    HisValAspGlyValProValLeuProGluSerGlnAlaGlyGlyGluValGlyValGlnGlnLeuGlyHisLeu
  ThrTyrThrGluTrpArgCysTrpArgSerProSerProGluValArgAM ValTrpArgSerPheAspMetSer

    AlaGlnGlyPheLysSerValValAlaValIleGlyLeuProAsnAspProSerValArgLeuHisGluAlaLeu
  GlyProGlyLeuGlnGluArgGlyArgArgHisArgThrAlaGlnArgProGluArgAlaProAlaArgGlyAla
ArgProArgAlaSerArgAlaTrpSerProSerSerAspCysProThrThrArgAlaCysAlaCysThrArgArg
AGGCCCAGGGCTTCAAGAGCGTGGTCGCCGTCATCGGACTGCCCAACGACCCGAGCGTGCGCCTGCACGAGGCGC     675
TCCGGGTCCCGAAGTTCTCGCACCAGCGGCAGTAGCCTGACGGGTTGCTGGGCTCGCACGCGGACGTGCTCCGCG
ProGlyProSerOP SerArgProArgArgOP ArgValAlaTrpArgGlySerArgAlaGlyAlaArgProAla
    GlyLeuAlaGluLeuAlaHisAspGlyAspAspSerGlnGlyValValArgAlaHisAlaGlnValLeuArgGlu
  AlaTrpProLysLeuLeuThrThrAlaThrMetProSerGlyLeuSerGlyLeuThrArgArgCysSerAlaSer

    GlyTyrThrAlaArgGlyThrLeuArgAlaAlaGlyTyrLysHisGlyGlyTrpHisAspValGlyPheTrpGln
  ArgIleHisArgAlaArgAspAlaAlaGlySerArgLeuGlnAlaArgGlyLeuAlaArgArgGlyValLeuAla
SerAspThrProArgAlaGlyArgCysGlyGlnProAlaThrSerThrGlyAlaGlyThrThrTrpGlySerGly
TCGGATACACCGCGCGCGGGACGCTGCGGGCAGCCGGCTACAAGCACGGGGGCTGGCACGACGTGGGGTTCTGGC     750
AGCCTATGTGGCGCGCGCCCTGCGACGCCCGTCGGCCGATGTTCGTGCCCCCGACCGTGCTGCACCCCAAGACCG
ArgIleCysArgAlaArgSerAlaAlaProLeuArgSerCysAlaArgProSerAlaArgArgProThrArgAla
    SerValGlyArgAlaProArgGlnProCysGlyAlaValLeuValProAlaProValValHisProGluProLeu
  ProTyrValAlaArgProValSerArgAlaAlaProAM LeuCysProProGlnCysSerThrProAsnGlnCys

    ArgAspPheGluLeuProAlaProProArgProValArgProValThrGlnIle
  AlaArgLeuArgAlaAlaGlyProAlaProProArgProAlaArgHisThrAsp
SerAlaThrSerSerCysArgProArgProAlaProSerGlyProSerHisArgSer
AGCGCGACTTCGAGCTGCCGGCCCCGCCCCGCCCCGTCCGGCCCGTCACACAGATCT                       807
TCGCGCTGAAGCTCGACGGCCGGGGCGGGGCGGGGCAGGCCGGGCAGTGTGTCTAGA
AlaArgSerArgAlaAlaProGlyAlaGlyGlyArgGlyAlaArgOP ValSerArg
    AlaValGluLeuGlnArgGlyArgGlyAlaGlyAspProGlyAspCysLeuAsp
  ArgSerLysSerSerGlyAlaGlyGlyArgGlyThrArgGlyThrValCysIle
```

DNA Sequence II

```
1   AGATCTGGAGCGACGTCCTGGGGGCCGGTCCGGTGCTGCCCGGGGACGACTTCTTCTCCC
    TCTAGACCTCGCTGCAGGACCCCCGGCCAGGCCACGACGGGCCCCTGCTGAAGAAGAGGG
```

1 BGLII XHOII, 2 DPNI SAU3A, 5 GSUI, 12 AATII ACYI, 13 MAEII, 17 APYI ECORII, 26 RSRII, 27 AVAII, 35 BBVI, 39 AVAI NCII SMAI, 40 NCII, 52 MBOII, 59 MNLI,

```
61  TCGGCGGCACCTCCATCTCGGCGTTGCGGGTGGTCTCGCGCATCCGCAAGGAACTCGGCG
    AGCCGCCGTGGAGGTAGAGCCGCAACGCCCACCAGAGCGCGTAGGCGTTCCTTGAGCCGC
```

66 HGICI, 70 MNLI, 97 FNUDII, 100 SFANI, 101 FOKI,

```
121 TGCCACTCCGGCTCGCCGTGATCTTCGAGACGCCGTCCCTGGAAGCGGTGGCCGAATCCG
    ACGGTGAGGCCGAGCGGCACTAGAAGCTCTGCGGCAGGGACCTTCGCCACCGGCTTAGGC
```

122 BGLI, 140 DPNI SAU3A, 142 MBOII, 149 ACYI HGAI TTH111I, 158 APYI ECORII, 169 CFRI GDIII, 174 HINFI, 180 RSAI,

```
181 TACTCCGCGAACTGAAGGGGACGTAGTAAAGAGGTGCCCGCCACCCGCTTTCGCAGAACA
    ATGAGGCGCTTGACTTCCCCTGCATCATTTCTCCACGGGCGGTGGGCGAAAGCGTCTTGT
```

185 FNUDII, 201 MAEII, 211 MNLI, 213 HGICI, 214 SDUI,

```
241 CCGAAGGAAGACCACACGTGAGCCCAGAACGACGCCCGGTCGAGATCCGTCCCGCCACCG
    GGCTTCCTTCTGGTGTGCACTCGGGTCTTGCTGCGGGCCAGCTCTAGGCAGGGCGGTGGC
```

247 MBOII, 254 AFLIII, 255 PMACI, 256 MAEII, 260 HGIJII SDUI, 271 ACYI HGAI, 275 NCII, 283 XHOII, 284 BINI DPNI SAU3A,

```
301 CCGCCGACATGGCGGCGGTCTGCGACATCGTCAATCACTACATCGAGACGAGCACGGTCA
    GGCGGCTGTACCGCCGCCAGACGCTGTAGCAGTTAGTGATGTAGCTCTGCTCGTGCCAGT
```

303 BGLI, 308 NLAIII, 324 TTH111I, 350 HGIAI SDUI, 357 HINCI I,

```
361 ACTTCCGTACGGAGCCGCAGACTCCGCAGGAGTGGATCGACGACCTGGAGCGCCTCCAGG
    TGAAGGCATGCCTCGGCGTCTGAGGCGTCCTCACCTAGCTGCTGGACCTCGCGGAGGTCC
```

367 RSAI, 380 HINFI, 394 BINI, 395 DPNI SAU3A, 404 APYI ECOR II, 405 GSUI, 409 HAEII, 413 MNLI, 414 GSUI, 416 APYI ECORII, 419 AVAII,

```
421 ACCGCTACCCCTGGCTCGTCGCCGAGGTGGAGGGCGTCGTCGCCGGCATCGCCTACGCCG
    TGGCGATGGGGACCGAGCAGCGGCTCCACCTCCCGCAGCAGCGGCCGTAGCGGATGCGGC
```

430 APYI ECORII, 444 MNLI, 450 MNLI, 453 ACYI, 454 HGAI, 462 NAEI, 466 SFANI, 477 NAEI,

```
481 GCCCCTGGAAGGCCCGCAACGCCTACGACTGGACCGTCGAGTCGACGGTGTACGTCTCCC
    CGGGGACCTTCCGGGCGTTGCGGATGCTGACCTGGCAGCTCAGCTGCCACATGCAGAGGG
```

484 APYI ECORII, 511 AVAII, 519 HINFI, 521 ACCI HINCII SALI, 530 RSAI, 532 MAEII,

```
541 ACCGGCACCAGCGGCTCGGACTGGGCTCCACCCTCTACACCCACCTGCTGAAGTCC ↑
    TGGCCGTGGTCGCCGAGCCTGACCCGAGGTGGGAGATGTGGGTGGACGACTTCAGGT ↑
```

544 HGICI, 549 NSPBII, 563 HGIJII GDUI, 572 MNLI, 578 TAQII, 583 BSPMI, 595 NCOI STYI, 596 NLAIII, 600 MNLI,

```
601 AGGCCCAGGGCTTCAAGAGCGTGGTCGCCGTCATCGGACTGCCCAACGACCCGAGCGTGC
    TCCGGGTCCCGAAGTTCTCGCACCAGCGGCAGTAGCCTGACGGGTTGCTGGGCTCGCACG
```

605 APYI ECORII, 650 AVAI,

```
661 GCCTGCACGAGGCGCTCGGATACACCGCGCGCGGGACGCTGCGGGCAGCCGGCTACAAGC
    CGGACGTGCTCCGCGAGCCTATGTGGCGCGCGCCCTGCGACGCCCGTCGGCCGATGTTCG
```

669 MNLI, 671 HAEII, 686 FNUDII, 687 BSSHII, 688 FNUDII, 690 FNUDII, 695 HGAI, 698 BBVI, 705 BBVI, 708 NAEI, 716 TTH111I I,

```
721 ACGGGGGCTGGCACGACGTGGGGTTCTGGCAGCGCGACTTCGAGCTGCCGGCCCCGCCCC
    TGCCCCCGACCGTGCTGCACCCCAAGACCGTCGCGCTGAAGCTCGACGGCCGGGGCGGGG
```

732 DRAIII, 736 MAEII, 749 BBVI, 753 FNUDII, 763 ALUI, 764 B BVI, 767 NAEI,

```
781 GCCCCGTCCGGCCCGTCACACAGATCT
    CGGGGCAGGCCGGGCAGTGTGTCTAGA
```

-continued

DNA Sequence II

795 MAEIII, 802 BGLII XHOII, 803 DPNI SAU3A,

We claim:

1. Phosphinothricin(PTC)-resistance gene obtainable by selecting *Streptomyces viridochromogenes* DSM 4112 for resistance to phosphinothricyl-alanyl-alanine (PTT), cutting with BamHI the total DNA from the resistant strains, cloning a fragment 4.0 kb in size, and selecting for PTT resistance.

2. The gene as claimed in claim 1, which has the restriction map shown in FIG. 1.

3. A bacterium transformed with the gene of claim 2.

4. A plant cell transformed with the gene of claim 2.

5. The gene as claimed in claim 1, comprising at least the positions 258–806 of the DNA sequence I:

DNA Sequence I

```
IleTrpSerAspValLeuGlyAlaGlyProValLeuProGlyAspAspPhePheSerLeuGlyGlyThrSerIle
AspLeuGluArgArgProGlyGlyArgSerGlyAlaAlaArgGlyArgLeuLeuLeuProArgArgHisLeuHis
ArgSerGlyAlaThrSerTrpGlyProValArgCysCysProGlyThrThrSerSerProSerAlaAlaProPro
AGATCTGGAGCGACGTCCTGGGGGCCGGTCCGGTGCTGCCCGGGGACGACTTCTTCTCCCTCGGCGGCACCTCCA     75
TCTAGACCTCGCTGCAGGACCCCCGGCCAGGCCACGACGGGCCCCTGCTGAAGAAGAGGGAGCCGCCGTGGAGGT
SerArgSerArgArgGlyProProArgAspProAlaAlaArgProArgSerArgArgGlyArgArgCysArgTrp
AspProAlaValAspGlnProGlyThrArgHisGlnGlyProValValGluGluGlyGluAlaAlaGlyGlyAsp
IleGlnLeuSerThrArgProAlaProGlyThrSerGlyProSerSerLysLysGluArgProProValGluMet

SerAlaLeuArgValValSerArgIleArgLysGluLeuGlyValProLeuArgLeuAlaValIlePheGluThr
LeuGlyValAlaGlyGlyLeuAlaHisProGlnGlyThrArgArgAlaThrProAlaArgArgAspLeuArgAsp
SerArgArgCysGlyTrpSerArgAlaSerAlaArgAsnSerAlaCysHisSerGlySerProOP SerSerArg
TCTCGGCGTTGCGGGTGGTCTCGCGCATCCGCAAGGAACTCGGCGTGCCACTCCGGCTCGCCGTGATCTTCGAGA     150
AGAGCCGCAACGCCCACCAGAGCGCGTAGGCGTTCCTTGAGCCGCACGGTGAGGCCGAGCGGCACTAGAAGCTCT
ArgProThrAlaProProArgAlaCysGlyCysProValArgArgAlaValGlyAlaArgArgSerArgArgSer
ArgArgGlnProHisAspArgAlaAspAlaLeuPheGluAlaHisTrpGluProGluGlyHisAspGluLeuArg
GluAlaAsnArgThrThrGluArgMetArgLeuSerSerProThrGlySerArgSerAlaThrIleLysSerVal

ProSerLeuGluAlaValAlaGluSerValLeuArgGluLeuLysGlyThrAM OC ArgGlyAlaArgHisPro
AlaValProGlySerGlyGlyArgIleArgThrProArgThrGluGlyAspValValLysArgCysProProPro
ArgArgProTrpLysArgTrpProAsnProTyrSerAlaAsnOP ArgGlyArgSerLysGluValProAlaThr
CGCCGTGGGTGGAAGCGGTGGCCGAATCCGTACTCCGCGAACTGAAGGGGACGTAGTAAAGAGGTGCCCGCCACC     225
GCGGCAGGGACCTTCGCCACCGGCTTAGGCATGAGGCGCTTGACTTCCCCTGCATCATTTCTCCACGGGCGGTGG
AlaThrGlyProLeuProProArgIleArgValGlyArgValSerProSerThrThrPheLeuHisGlyGlyGly
ArgGlyGlnPheArgHisGlyPheGlyTyrGluAlaPheGlnLeuProArgLeuLeuSerThrGlyAlaValArg
GlyAspArgSerAlaThrAlaSerAspThrSerArgSerSerPheProValTyrTyrLeuProAlaArgTrpGly

LeuSerGlnAsnThrGluGlyArgProHisValSerProGluArgArgProValGluIleArgProAlaThrAla
AlaPheAlaGluHisArgArgLysThrThrArgGluProArgThrThrProGlyArgAspProSerArgHisArg
ArgPheArgArgThrProLysGluAspHisThrOP AlaGlnAsnAspAlaArgSerArgSerValProProPro
CGCTTTCGCAGAACACCGAAGGAAGACCACACGTGAGCCCAGAACGACGCCCGGTCGAGATCCGTCCCGCCACCG     300
GCGAAAGCGTCTTGTGGCTTCCTTCTGGTGTGCACTCGGGTCTTGCTGCGGGCCAGCTCTAGGCAGGGCGGTGGC
AlaLysAlaSerCysArgLeuPheValValArgSerGlyLeuValValGlyProArgSerGlyAspArgTrpArg
LysArgLeuValGlyPheSerSerTrpValHisAlaTrpPheSerAlaArgAspLeuAspThrGlyGlyGlyGly
SerGluCysPheValSerProLeuGlyCysThrLeuGlySerArgArgGlyThrSerIleArgGlyAlaValAla

AlaAspMetAlaAlaValCysAspIleValAsnHisTyrIleGluThrSerThrValAsnPheArgThrGluPro
ArgArgHisGlyGlyGlyLeuArgHisArgGlnSerLeuHisArgAspGluHisGlyGlnLeuProTyrGlyAla
ProProThrTrpArgArgSerAlaThrSerSerIleThrThrSerArgArgAlaArgSerThrSerValArgSer
CCGCCGACATGGCGGCGGTCTGCGACATCGTCAATCACTACATCGAGACGAGCACGGTCAACTTCCGTACGGAGC     375
GGCGGCTGTACCGCCGCCAGACGCTGTAGCAGTTAGTGATGTAGCTCTGCTCGTGCCAGTTGAAGGCATGCCTCG
ArgArgCysProProProArgArgCysArgOP AspSerCysArgSerSerCysProOP SerGlyTyrProAla
GlyValHisArgArgAspAlaValAspAspIleValValAspLeuArgAlaArgAspValGluThrArgLeuArg
AlaSerMetAlaAlaThrGlnSerMetThrLeuOP AM MetSerValLeuValThrLeuLysArgValSerGly

GlnThrProGlnGluTrpIleAspAspLeuGluArgLeuGlnAspArgTyrProTrpLeuValAlaGluValGlu
AlaAspSerAlaGlyValAspArgArgProGlyAlaProProGlyProLeuProLeuAlaArgArgArgGlyGly
ArgArgLeuArgArgSerGlySerThrThrTrpSerAlaSerArgThrAlaThrProGlySerSerProArgTrp
CGCAGACTCCGCAGGAGTGGATCGACGACCTGGAGCGCCTCCAGGACCGCTACCCCTGGCTCGTCGCCGAGGTGG     450
GCGTCTGAGGCGTCCTCACCTAGCTGCTGGACCTCGCGGAGGTCCTGGCGATGGGGACCGAGCAGCGGCTCCACC
AlaSerGluAlaProThrSerArgArgGlyProAlaGlyGlyProGlySerGlyArgAlaArgArgArgProPro
LeuSerArgLeuLeuProAspValValGlnLeuAlaGluLeuValAlaValGlyPRoGluAspGlyLeuHisLeu
CysValGlyCysSerHisIleSerSerArgSerArgArgTrpSerArgAM GlyGlnSerThrAlaSerThrSer
```

-continued

DNA Sequence I

```
 GlyValValAlaGlyIleAlaTyrAlaGlyProTrpLysAlaArgAsnAlaTyrAspTrpThrValGluSerThr
 GlyArgArgArgArgHisArgLeuArgArgProLeuGluGlyProGlnArgLeuArgLeuAspArgArgValAsp
ArgAlaSerSerProAlaSerProThrProAlaProGlyArgProAlaThrProThrThrGlyProSerSerArg
AGGGCGTCGTCGCCGGCATCGCCTACGCCGGCCCCTGGAAGGCCCGCAACGCCTACGACTGGACCGTCGAGTCGA   525
TCCCGCAGCAGCGGCCGTAGCGGATGCGGCCGGGGACCTTCCGGGCGTTGCGGATGCTGACCTGGCAGCTCAGCT
ProArgArgArgArgCysArgArgArgArgGlyArgSerProGlyCysArgArgArgSerSerArgArgThrSer
 AlaAspAspGlyAlaAspGlyValGlyAlaGlyProLeuGlyAlaValGlyValValProGlyAspLeuArgArg
 ProThrThrAlaProMetAlaAM AlaProGlyGlnPheAlaArgLeuAlaAM SerGlnValThrSerAspVal

 ValTyrValSerHisArgHisGlnArgLeuGlyLeuGlySerThrLeuTyrThrHisLeuLeuLysSerMetGlu
 GlyValArgLeuProProAlaProAlaAlaArgThrGlyLeuHisProLeuHisProProAlaGluValHisGly
ArgCysThrSerProThrGlyThrSerGlySerAspTrpAlaProProSerThrProThrCysOP SerProTrp
CGGTGTACGTCTCCCACCGGCACCAGCGGCTCGGACTGGGCTCCACCCTCTACACCCACCTGCTGAAGTCCATGG   600
GCCACATGCAGAGGGTGGCCGTGGTCGCCGAGCCTGACCCGAGGTGGGAGATGTGGGTGGACGACTTCAGGTACC
ProThrArgArgGlyGlyAlaGlyAlaAlaArgValProSerTrpGlyArgCysGlyGlyAlaSerThrTrpPro
 HisValAspGlyValProValLeuProGluSerGlnAlaGlyGlyGluValGlyValGlnGlnLeuGlyHisLeu
 ThrTyrThrGluTrpArgCysTrpArgSerProSerProGluValArgAM ValTrpArgSerPheAspMetSer

 AlaGlnGlyPheLysSerValValAlaValIleGlyLeuProAsnAspProSerValArgLeuHisGluAlaLeu
 GlyProGlyLeuGlnGluArgGlyArgArgHisArgThrAlaGlnArgProGluArgAlaProAlaArgGlyAla
ArgProArgAlaSerArgAlaTrpSerProSerSerAspCysProThrThrArgAlaCysAlaCysThrArgArg
AGGCCCAGGGCTTCAAGAGCGTGGTCGCCGTCATCGGACTGCCCAACGACCCGAGCGTGCGCCTGCACGAGGCGC   675
TCCGGGTCCCGAAGTTCTCGCACCAGCGGCAGTAGCCTGACGGGTTGCTGGGCTCGCACGCGGACGTGCTCCGCG
ProGlyProSerOP SerArgProArgArgOP ArgValAlaTrpArgGlySerArgAlaGlyAlaArgProAla
 GlyLeuAlaGluLeuAlaHisAspGlyAspAspSerGlnGlyValValArgAlaHisAlaGlnValLeuArgGlu
 AlaTrpProLysLeuLeuThrThrAlaThrMetProSerGlyLeuSerGlyLeuThrArgArgCysSerAlaSer

 GlyTyrThrAlaArgGlyThrLeuArgAlaAlaGlyTyrLysHisGlyGlyTrpHisAspValGlyPheTrpGln
 ArgIleHisArgAlaArgAspAlaAlaGlySerArgLeuGlnAlaArgGlyLeuAlaArgArgGlyValLeuAla
SerAspThrProArgAlaGlyArgCysGlyGlnProAlaThrSerThrGlyAlaGlyThrThrTrpGlySerGly
TCGGATACACCGCGCGCGGGACGCTGCGGGCAGCCGGCTACAAGCACGGGGGCTGGCACGACGTGGGGTTCTGGC   750
AGCCTATGTGGCGCGCGCCCTGCGACGCCCGTCGGCCGATGTTCGTGCCCCCGACCGTGCTGCACCCCAAGACCG
ArgIleCysArgAlaArgSerAlaAlaProLeuArgSerCysAlaArgProSerAlaArgArgProThrArgAla
 SerValGlyArgAlaProArgGlnProCysGlyAlaValLeuValProAlaProValValHisProGluProLeu
 ProTyrValAlaArgProValSerArgAlaAlaProAM LeuCysProProGlnCysSerThrProAsnGlnCys

 ArgAspPheGluLeuProAlaProProArgProValArgProValThrGlnIle
 AlaArgLeuArgAlaAlaGlyProAlaProProArgProAlaArgHisThrAsp
SerAlaThrSerSerCysArgProArgProAlaProSerGlyProSerHisArgSer
AGCGCGACTTCGAGCTGCCGGCCCCGCCCCGCCCCGTCCGGCCCGTCACACAGATCT   807
TCGCGCTGAAGCTCGACGGCCGGGGCGGGGCGGGGCAGGCCGGGCAGTGTGTCTAGA
AlaArgSerArgAlaAlaProGlyAlaGlyGlyArgGlyAlaArgOP ValSerArg
 AlaValGluLeuGlnArgGlyArgGlyAlaGlyAspProGlyAspCysLeuAsp
 ArgSerLysSerSerGlyAlaGlyGlyArgGlyThrArgGlyThrValCysIle
```

6. A bacterium transformed with the gene of claim 5.

7. A plant cell transformed with the gene of claim 5.

8. A bacterium transformed with the gene of claim 1.

9. A plant cell transformed with the gene of claim 1.

10. A process for the selective acetylation of the $NH_2$-group of the L-form of racemic PTC which comprises contacting racemic PTC with (a) a cell expressing a phosphinothricin (PTC)-resistance gene, wherein said gene is obtainable by selecting *Streptomyces viridochromogenes* DSM 4112 for resistance to phosphinothricyl-alanyl-alanine (PTT), cutting with BamHI the total DNA from the resistant strains, cloning a fragment 4.0 kb in size, and selecting for PTT resistance, or (b) the enzyme encoded by said gene and fractionating the D-form and the acylated L-form of PTC.

11. The process of claim 10 wherein said gene has the restriction map shown in FIG. 1.

12. The process of claim 10 wherein said gene has the DNA sequence I, positions 258–806.

* * * * *

UNITED STATES PATENT AND TRADEMARK OFFICE

CERTIFICATE OF CORRECTION

PATENT NO. : 5,273,894

DATED : December 28, 1993

INVENTOR(S) : Eckhard STRAUCH et al.

It is certified that error appears in the above-indentified patent and that said Letters Patent is hereby corrected as shown below:

columns 13-14, line 225 of the sequence listing, 7th, 8th, and 9th letters (reading for the left margin) change "GGG" to --CCC--.

column 14, line 453 of the sequence, letter 20 (reading from the right margin), change "R" to --r--.

Signed and Sealed this

Twenty-first Day of March, 1995

Attest:

BRUCE LEHMAN

Attesting Officer

Commissioner of Patents and Trademarks